United States Patent [19]
Edwards

[11] 4,334,882
[45] Jun. 15, 1982

[54] DETERMINATION OF PYRITE AND SIDERITE CONTENT OF FORMATION DEPOSITS

[75] Inventor: Joseph T. Edwards, Grand Prairie, Tex.

[73] Assignee: Mobil Oil Corporation, New York, N.Y.

[21] Appl. No.: 249,778

[22] Filed: Apr. 1, 1981

[51] Int. Cl.$^3$ ........................... G01J 3/30; G01N 3/24
[52] U.S. Cl. .............................. 23/230 R; 23/230 EP; 23/230 PC; 356/316; 166/252
[58] Field of Search ........ 23/230 R, 230 PC, 230 EP; 166/252; 356/316; 324/376

[56] References Cited

U.S. PATENT DOCUMENTS 3,302,101  1/1967  Glanville ............................ 324/376
4,225,314  9/1980  Macourt ............................. 356/316

*Primary Examiner*—Michael S. Marcus
*Attorney, Agent, or Firm*—Charles A. Huggett; Michael G. Gilman; Frank J. Kowalski

[57] ABSTRACT

A method for determination of pyrite and sidermite content in core samples is disclosed wherein the method involves a two-step digestion of the minerals in hydrochloric and nitric acids and analysis of the solutions using an inductively coupled plasma atomic emission spectrometer.

3 Claims, No Drawings

DETERMINATION OF PYRITE AND SIDERITE CONTENT OF FORMATION DEPOSITS

BACKGROUND OF THE INVENTION

In oil exploration after a well has been drilled, various well logs are taken to determine porosity of the well and the location of oil or hydrocarbon zones. Spontaneous potential (SP) logs are taken to determine porous zones. Resistivity logs are taken to determine oil or hydrocarbon zones within the porous zones. Normally, hydrocarbon and water interfaces are determined through the resistivity logs since oil and gas have appreciably higher resistivity than that of formation waters. A formation mineral pyrite ($FeS_2$) has a resistivity similar to that of formation water. When pyrite is present in a hydrocarbon zone, a resistivity log may give an erroneously low indication of hydrocarbon content.

A prior art method used to distinguish hydrocarbon zones having pyrite from water zones has been to take an additional log, a density log. Pyrite has a significantly higher density than formation water and the density log can be used to determine whether a low resistivity porous zone is formation water or hydrocarbons with pyrite. However, when an oil zone is near a pyrite zone, siderite ($FeCO_3$) may also be present. Siderite is essentially nonconductive and presents no false readings on a resistivity log, however siderite has a high density like pyrite. A hydrocarbon zone containing pyrite and a water zone containing siderite may have similar resistivity and density log responses. Thus, when pyrite and siderite are present in water and hydrocarbon bearing zones a combination of density and resistivity logs cannot accurately identify water/oil content.

SUMMARY OF THE INVENTION

The present invention discloses a method for the determination of pyrite and siderite content of core material to permit correction of resistivity logs for the presence of pyrite. A portion of a crushed core sample is chemically treated with hydrochloric acid (HCL) to remove all iron except for that contained as ferrous sulfide. The acid solution is filtered and saved. The solid is then treated with nitric acid ($HNO_3$) to dissolve the ferrous sulfide, and that solution is filtered and saved. An inductively coupled plasma spectra is used to analyze the hydrochloric and nitric solutions to determine the percent of iron in each sample. In further embodiment of the present invention the nitric acid and hydrochloric acid solutions may be treated with barium chloride to determine the percent of sulphur in each of the solutions as a verification of the percent of pyrite and siderite in the original sample.

DESCRIPTION OF THE PREFERRED EMBODIMENT

When a resistivity log is taken in an oil well, normally oil and water interfaces may be selected and zones having a predetermined resistivity are classified as hydrocarbon-bearing zones. If pyrite ($FeS_2$) is present in the hydrocarbon zone, a lower resistivity, such as that of formation water, is indicated. As a result, a smaller hydrocarbon zone than really exists is also indicated. Traditionally, density logs have been taken to determine the zones whose resistivity is caused by the presence of pyrite and thus to correct the resistivity logs. When siderite ($FeCO_3$) and pyrite are present together, density logs cannot be used effectively to correct for this "pyrite effect". This is due to the fact that a hydrocarbon zone having pyrite in the formation and a water zone having siderite may have similar resistivity and density log responses. The method of the present invention lies in an accurate laboratory determination of pyrite and siderite content of core material.

A dried core sample to be tested is taken and a small sample of accurately weighed crushed sample is placed in a beaker. In the preferred embodiment approximately 10 grams is taken, however any size sample may be used. A predetermined amount, preferably 80 milliliters, of deoxygenated 5% hydrochloric acid (HCl) is added to the beaker containing the sample. The hydrochloric acid may be deoxygenated by bubbling nitrogen through it, however any common accepted practice may be used. The beaker is covered and placed in the water bath at an elevated temperature, preferably 90° C., for two hours. An additional amount, preferably 20 milliliters, of 5% hydrochloric acid is added to insure complete dissolution of carbonate minerals. After cooling, the sample is filtered and washed thoroughly on a Millipore filter, preferably 0.45 micrometers. The hydrochloric acid solution is transferred to a 500 milliliter volumetric flask and brought to volume with distilled water and set aside for analysis.

The undissolved portion of the sample is quantitatively washed from the filter and returned to the beaker. A predetermined amount, preferably 80 milliliters, of 20% nitric acid is added. If the sample contains abundant amounts of pyrite the addition of the nitric acid in steps may be required. The mixture is allowed to react slowly at room temperature until most of the pyrite has dissolved. An additional amount, preferably 40 milliliters of concentrated nitric acid is added in the undissolved sample, and is heated in a water bath for preferably four hours although any amount of time to assure total dissolution may be used. After cooling the sample is filtered and washed and the solution is transferred to an additional 500 milliliter volumetric flask and brought to volume with distilled water and set aside.

The undissolved portion of the sample is washed in an evaporating dish, dried, and weighed, and the percent weight loss is recorded. The drying step be may done in any suitable manner, however elevating the sample temperature to is 90° C. preferred to reduce drying time.

The 500 milliliters of hydrochloric acid solution and 500 milliliters of nitric acid solution are analyzed using an inductively coupled plasma spectrometer to determined iron content. Minor elements such as magnesium and calcium and the trace elements of vanadium, manganese, cobalt, nickel, copper, zinc, arsenic and barium are also determined. The concentration of the elements in the hydrochloric acid and nitric acid solutions are translated into concentrations (in parts per million) of the elements in the rock by the formula $$C = \frac{\text{(Dilution Factor)} \times \text{(Milligrams/Liter in Solution)} \times 500}{\text{(Sample Weight)}}$$

where
C = the concentration of iron in parts per million
Dilution Factor = The dilution of the sample solution for ICP analysis
Milligrams/Liter in Solution = The amount determined from ICP analysis and Sample Weight = The original weight of the sample taken from the core.

The concentration values for the hydrochloric and nitric acid solutions are reported separately and concentrations for trace elements should have a detection limit of approximately 10 parts/million.

As a further embodiment of the present invention, a gravimetric sulfur determination may be performed to determine the sulfur content in the hydrochloric and nitric acid solutions as a verification of the iron present in the nitric acid solution. A predetermined amount of the hydrochloric solution, preferably 100 milliliters is pipetted into a beaker and an amount, preferably 10 millimeters of 1 M $BaCl.2H_2O$ is added and allowed to stand for one hour although any amount of time to assure reaction of barium and sulfur may be used. The precipitate barium sulfate, ($BaSO_4$), is filtered on a weighed Millipore filter preferably 0.45 micrometers washed, dried, and weighed. The percent sulfur, from the rock due to hydrochloric dissolution is calculated by the following formula.

$$S(\%) = \frac{(\text{Weight } BaSO_4) \times (68.68)}{(\text{Sample Weight})}$$

where
S = % sulfur
Weight $BaSO_4$ = The atomic weight of barium sulfate
Sample Weight = weight of the original sample taken from the core.

68.68 is determined by taking the formula weight of sulfur which is 32.06 and dividing this by the atomic weight of barium sulphate = 233.39 which in sulfur a 13.7366% weight of barium sulphate. Since the sampling is 100 milliliters of 500 milliliter total sample the 13.7366% weight would be multiplied by 5 to get 68.68%.

To determine the amount of sulfur in the nitric acid solution a portion of the solution, preferably 100 milliliters, is evaporated to near dryness. To remove nitrates a predetermined amount, preferably 25 milliliters, of concentrated hydrochloric acid is added and the solution is again evaporated to near dryness. This is repeated several times; in the preferred embodiment three times is sufficient. After the final evaporation, a predetermined amount, preferably 500 milliliters, of concentrated hydrochloric acid and 100 milliliters of distilled water are added. The solution is heated near boiling and a predetermined amount, preferably 10 milliliters, of 1 M $BaCl.2H_2O$ is added and the heating is continued for a minimum of two hours. The precipitate is filtered, washed, dried and weighed. This filtering may be done on a Millipore filter if care is taken in the drying step. However, a Selas porcelain crucible with fine porosity is preferred since the precipitate can then be heated conveniently to temperatures such as 100° C. The weight percent is calculated and reported independently for the hydrochloric and nitric acid solutions.

The method of the present invention comprises taking a core sample from an oil well and grinding a small portion of it for analysis. The sample is first treated with hydrochloric acid to remove the presence of iron due to siderite and other iron containing minerals. Pyrite ($FeS_2$) is not soluble in hydrochloric acid and remains in the sample after the hydrochloric solution has been washed out. The washed sample is then treated with nitric acid in which pyrite is soluble. An inductively coupled plasma spectrometer is performed on the hydrochloric and nitric acid solutions to determine the concentration of iron in each of the solutions. The concentration of iron in the hydrochloric solution will be primarily due to siderite whereas the concentration of iron in the nitric acid solution will be due exclusively to pyrite. Thus, the concentrations of pyrite and siderite in the core sample may be determined and correction factors for resistivity logs may be made.

Although the present invention has been described by way of preferred embodiment, it is to be understood that the present invention is not to be limited thereto, but only by the scope of the following claims.

What is claimed is:

1. A method for determining the concentration of pyrite in a sample comprising the steps of:
    placing said sample in a hydrochloric acid solution;
    dissolving a portion of said sample in said hydrochloric acid solution;
    removing said sample from said hydrochloric acid solution;
    placing said sample in a nitric acid solution;
    dissolving a second portion of said sample in said nitric acid solution;
    removing said sample from said nitric acid solution; and
    performing an inductively coupled plasma spectrometer analysis of said nitric acid solution and said hydrochloric acid solution to determine the concentration of iron in each solution.

2. The method according to claim 1 wherein said step of placing said sample in a solution includes the steps of:
    adding 80 milliliters of deoxygenated 5% hydrochloric acid to said sample;
    placing said sample and said hydrochloric acid solution in a water bath for one hour; and
    adding 20 milliliters of 5% hydrochloric acid solution to said sample and said hydrochloric acid solution.

3. The method according to claim 1 wherein the step of placing said sample in a nitric acid solution includes the steps of:
    adding the sample of 80 milliliters of 20% nitric acid;
    allowing the mixture to react slowly at room temperature;
    adding 40 milliliters of concentrated nitric acid; and
    heating said sample and said nitric acid solution in the water bath for four hours.

* * * * *